United States Patent [19]

Slater

[11] Patent Number: 4,625,571
[45] Date of Patent: Dec. 2, 1986

[54] GRAB SAMPLER

[75] Inventor: Brian G. Slater, Rochester, England

[73] Assignee: British Petroleum Company, London, England

[21] Appl. No.: 435,630

[22] Filed: Oct. 20, 1982

[30] Foreign Application Priority Data

Oct. 31, 1981 [GB] United Kingdom ............... 8132869

[51] Int. Cl.⁴ .............................................. G01N 1/14
[52] U.S. Cl. ................................................. 73/863.84
[58] Field of Search ........... 73/863.71, 863.72, 863.73, 73/863.81, 863.82, 863.83, 863.84, 863.85, 863.86, 864.34, 864.63, 864.73, 864.74

[56] References Cited

U.S. PATENT DOCUMENTS

| | | | |
|---|---|---|---|
| 2,872,817 | 2/1959 | Pitts ................................. | 73/863.84 |
| 3,087,334 | 4/1963 | Brown .............................. | 73/863.83 |
| 3,412,613 | 11/1968 | Brown et al. ..................... | 73/864.74 |
| 3,812,722 | 5/1974 | Soudelier ......................... | 73/863.84 |
| 4,350,051 | 9/1982 | Thompson ....................... | 73/864.74 |
| 4,403,518 | 9/1983 | Weiker ............................. | 73/864.34 |

FOREIGN PATENT DOCUMENTS

| | | |
|---|---|---|
| 846589 | 8/1960 | United Kingdom . |
| 1224522 | 3/1971 | United Kingdom . |
| 2094266 | 9/1982 | United Kingdom . |

*Primary Examiner*—S. Clement Swisher
*Attorney, Agent, or Firm*—Brooks Haidt Haffner & Delahunty

[57] ABSTRACT

This invention relates to a grab sampler for liquids especially for crude oil flowing through pipelines. The sampler has a set of concentric tubular members including an outer body with an inlet and outlet, and a sleeve and a hollow piston which are respectively axially slideable within the body and the sleeve. The piston has an internal non-return valve as its base. The sleeve, the piston base and the body are capable of defining a sample chamber so as to trap a sample of the liquid flowing through the pipeline. Application of pressure on the piston displaces the trapped sample through the nonreturn valve to the inside of the piston and is recovered therefrom by sample removal means.

17 Claims, 4 Drawing Figures

GRAB SAMPLER

The present invention relates to a sampler for liquids, in particular to a sampler for crude oil flowing through pipelines.

In industries in which large quantities of liquids are pumped through pipelines, eg the petroleum industry, it is necessary for a representative sample of the liquid to be retrieved at regular intervals for the purposes of routine analysis. Recently, automatic samplers have been used for this purpose. Various forms of these samplers have been used to achieve this type of monitoring function, and they all rely on the same principle of removing a small volume, herein called a 'grab', from the pipeline or from a by-pass loop at frequent intervals and accumulating these grabs in a receiver.

The present invention is primarily, but not exclusively, directed to the sampling of wet crude oil for the purpose of determining the water content thereof. The measurement of the water content of crude oil for fiscal and oil loss accounting purposes has become extremely important with the increase in the cost of crude oil. The samplers used hitherto for this purpose do not satisfactorily meet one or more of the following criteria:

(a) structural robustness especially in a petrochemical environment;

(b) ease of sampler insertion into a pipeline in service;

(c) ability to operate up to a pressure of class 1500 duty (ANSI) and at elevated temperatures;

(d) ability to operate without dependence on pipeline flow rate;

(e) serviceability in the field, eg by removal of components 'in situ' for servicing;

(f) collection of samples in an isokinetic manner;

(g) ability to operate at a sample rate of 1 per second;

(h) flexibility in terms of the choice of power source for actuation;

(i) ability to operate within an environment of abrasive liquids eg crude oil containing sediments; and (j) in-line operability avoiding use of external sample lines or by-pass loops and their attendant problems.

It is an object of the present invention to mitigate the problems encountered with prior art samplers.

Accordingly, the present invention is a device for sampling liquid flowing through a pipeline, said device being adapted to be inserted into the pipeline and comprising:

A. a set of concentric tubular members made up of (1) an outer cylindrical body having a radially orientated liquid inlet and liquid outlet adjacent to the base thereof, (2) a sleeve mounted within and axially slideable with respect to the outer cylindrical body, and (3) a hollow piston mounted within and axially slideable with respect to the sleeve, wherein (a) the sleeve is adapted to define a liquid-tight chamber between the walls thereof, the base portion of the body and the piston, and is capable of trapping a sample of liquid within said chamber, (b) the piston is provided at the base thereof with an internal non-return valve and is adapted to apply pressure to the trapped sample thereby displacing the sample through the valve into the inside of the piston, and (c) the inside of the piston is connected to sample removal means for removal of the sample therein, and B. actuator means for sequentially lowering first the sleeve and then the piston so as to isolate and remove a sample of liquid.

The inlet and outlet in the cylindrical body are preferably transversely orientated.

In the normal open position of the inlet and outlet when liquid flows freely therethrough, the sleeve and the piston are held above the body inlet and outlet by the actuator means. Operation of the actuator means causes the sleeve and the piston successively to descend towards the base of the body. The descent of the sleeve initially seals off a chamber from the pipeline by closing the body inlet and the outlet, thereby trapping a sample within the chamber. Fractionally thereafter the piston descends applying pressure to the sample thereby displacing it through the non-return valve into the inside of the piston, and at the same time pumping an aliquot of the sample out through the sample removal means. On completion of this operation, the actuating force is reversed causing the sleeve and the piston to retract to their normal position above the body inlet and the body outlet, thereby restoring flow through the body.

The actuation of the sleeve and piston in a sequential manner may be achieved by either a pneumatic, electrical or hydraulic actuator. In one method the sleeve and the piston may be driven by an electric motor and cams to achieve the necessary independant operation. In a preferred embodiment a single stroke by the actuator means is converted into a differential action by means of a compression spring acting between the sleeve and the piston so as to form a lost-motion mechanism. Suitably the compression spring is located between collars attached to or shoulders formed on the sleeve and the piston. In the normal open position of the body inlet and outlet the sleeve and the piston are held in position above the inlet and outlet by means of a cage or yoke engaging with the sleeve, e.g. beneath a sleeve collar or shoulder, and lifting the sleeve so as to compress the spring against the piston, the piston being restrained from upward movement by means of a stop member on the upper portion of the outer body. In operation of the sampling device the actuator means initiates a downward movement of the cage thus releasing the sleeve and allowing it to move downwards under the action of the compression spring, instantaneously closing the body inlet and outlet and trapping a sample within the chamber so formed, the piston remaining against the stop member meanwhile. Further downward movement of the cage causes this to engage with the top of the piston, forcing this downwards away from the stop member so as to apply pressure to the sample in the chamber thereby displacing it through the non-return valve into the inside of the piston. This downward movement of the piston pumps an aliquot of the sample out through the sample removal means. Thereafter the actuator mechanism is reversed and the cage moves upwards, engaging again with the sleeve and moving this upwards into the open position, at the same time lifting the piston via the compression spring up to the stop member, and finally re-compressing the spring. The sleeve and the piston are then in the normal open position such that the sleeve, the piston and the non-return valve form a continuous flush surface along their respective bases. Once the sleeve and the piston have retracted the inlet and outlet are again open for continuation of liquid flow through the body. The operation may be repeated according to a predetermined rate for continuous sampling.

The non-return valve in the piston is normally retained in a closed positon suitably by means of a spring. The bias of the spring is overcome by the downward movement of the piston causing pressure to be applied on the trapped sample within the chamber thereby enabling the sample to flow through the valve into the inside of the piston. The non-return valve is preferably provided with an elongated valve stem extending through the length of the piston so as to form an internal annulus within the piston. In this case the retaining means for the non-return valve eg the spring is connected to the elongated stem so as to transmit the closure function to the valve through the stem. The function of the elongated stem is to facilitate lifting of the non-return valve thereby enabling the system to be cleaned without removing the entire sampler from the pipeline.

The sample removal means suitably comprises a relief valve which can be set so that its relief pressure is above the highest expected line pressure, thereby preventing continuous delivery of liquid from the pipeline through the device, but below the pressure exerted by the piston on the sample. In one embodiment the non-return valve in the piston also operates as the relief valve, but it is preferred to provide a separate relief valve which is suitably externally placed with respect to the outer cylindrical body, facilitating 'in-situ' servicing of the valve. The relief valve can be connected to a conventional sample collector. A shut-off valve may be provided between the inside of the piston and the relief valve to facilitate servicing of the relief valve 'in-situ'.

The sealing of the device against the pipeline pressure may be achieved by means of primary conventional seals provided at the base of both the sleeve and the piston. Secondary seals may also be provided at the top of the sleeve and the piston and at the base of the body where the sleeve comes into contact therewith. The seals are conventionally packed glands which can accommodate the reciprocating motion of the sleeve and piston and may have in addition adjustable stuffing boxes. Several additional features may be added to the device of the present invention. For example, the non-return valve and the piston may each be removably mounted and the sleeve may be adapted to be locked in its descended position. This will effectively shut off the pipeline pressure to the remainder of the unit and will therefore allow the removal of the non-return valve and the piston for servicing 'in situ'. Moreover, the body inlet is preferably provided with a flow straightening mouthpiece to enable extraction of streamlined samples without unduly disturbing flow patterns eg without allowing partial separation of the phases to take place.

A specific embodiment of the present invention is illustrated in the accompanying drawings in which.

Figure 1:
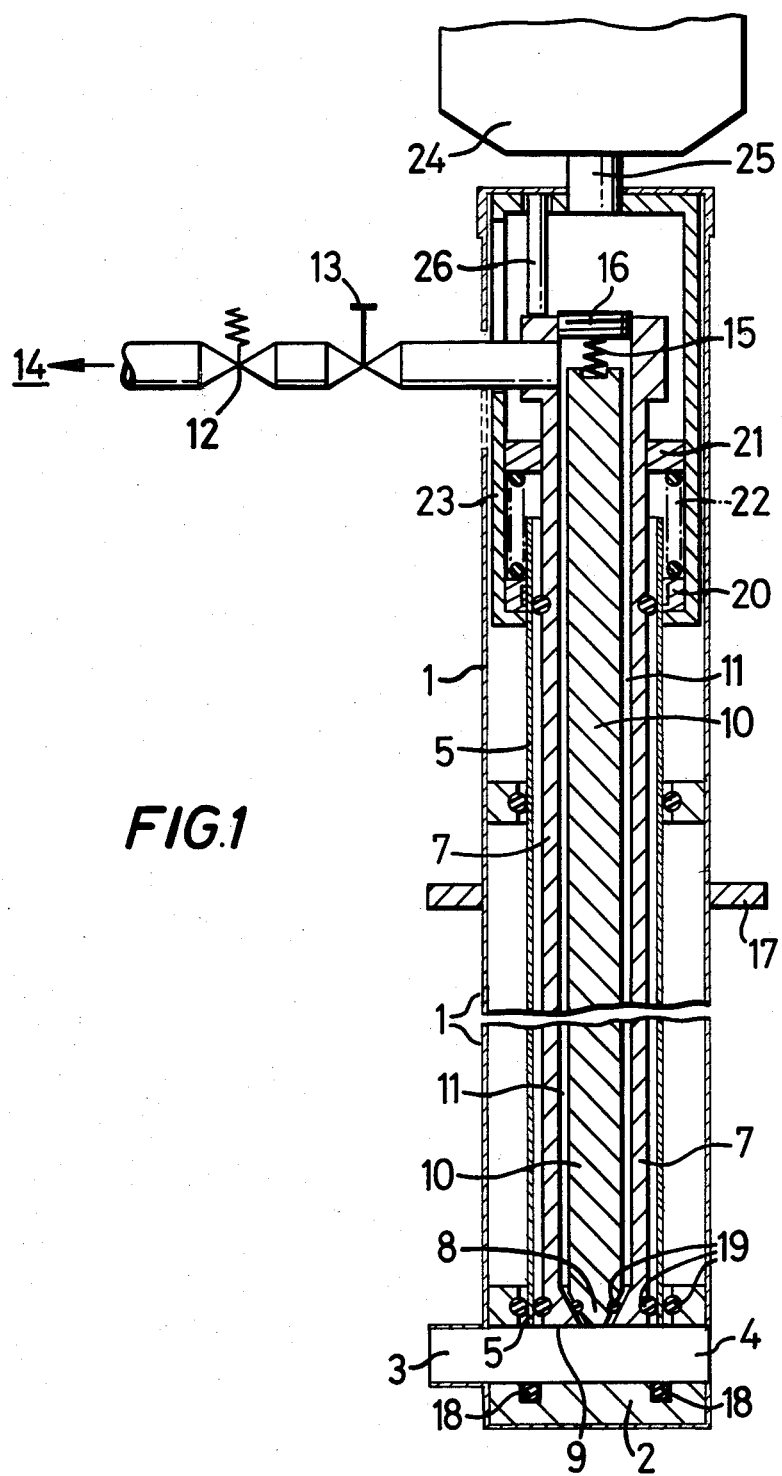
FIG. 1 represents a sectional view of the device in its normal position with the inlet and the outlet open.
Figure 2:
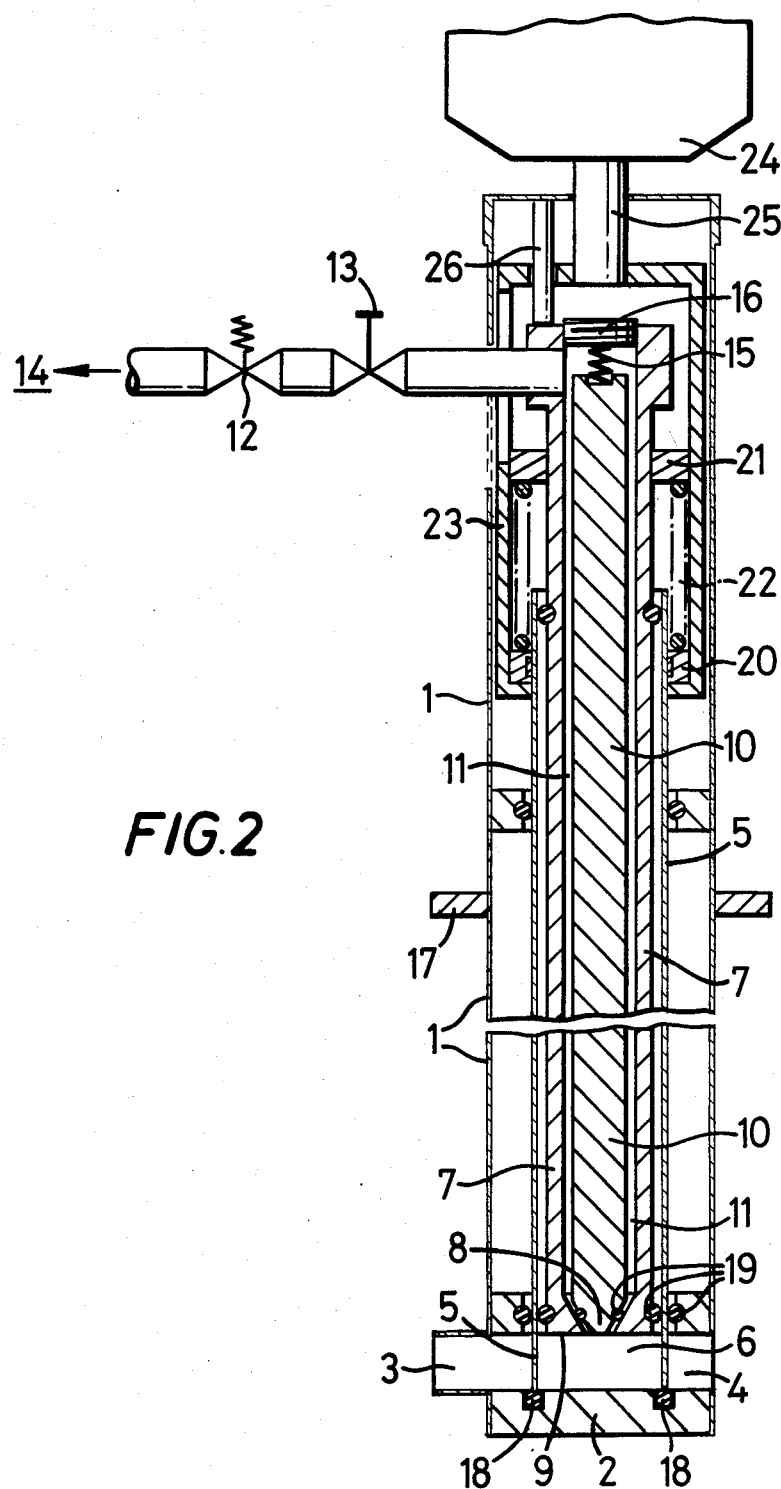
FIG. 2 represents a sectional view of the device with the inlet and outlet closed by the sleeve but with the piston still in the 'up' position.
Figure 3:
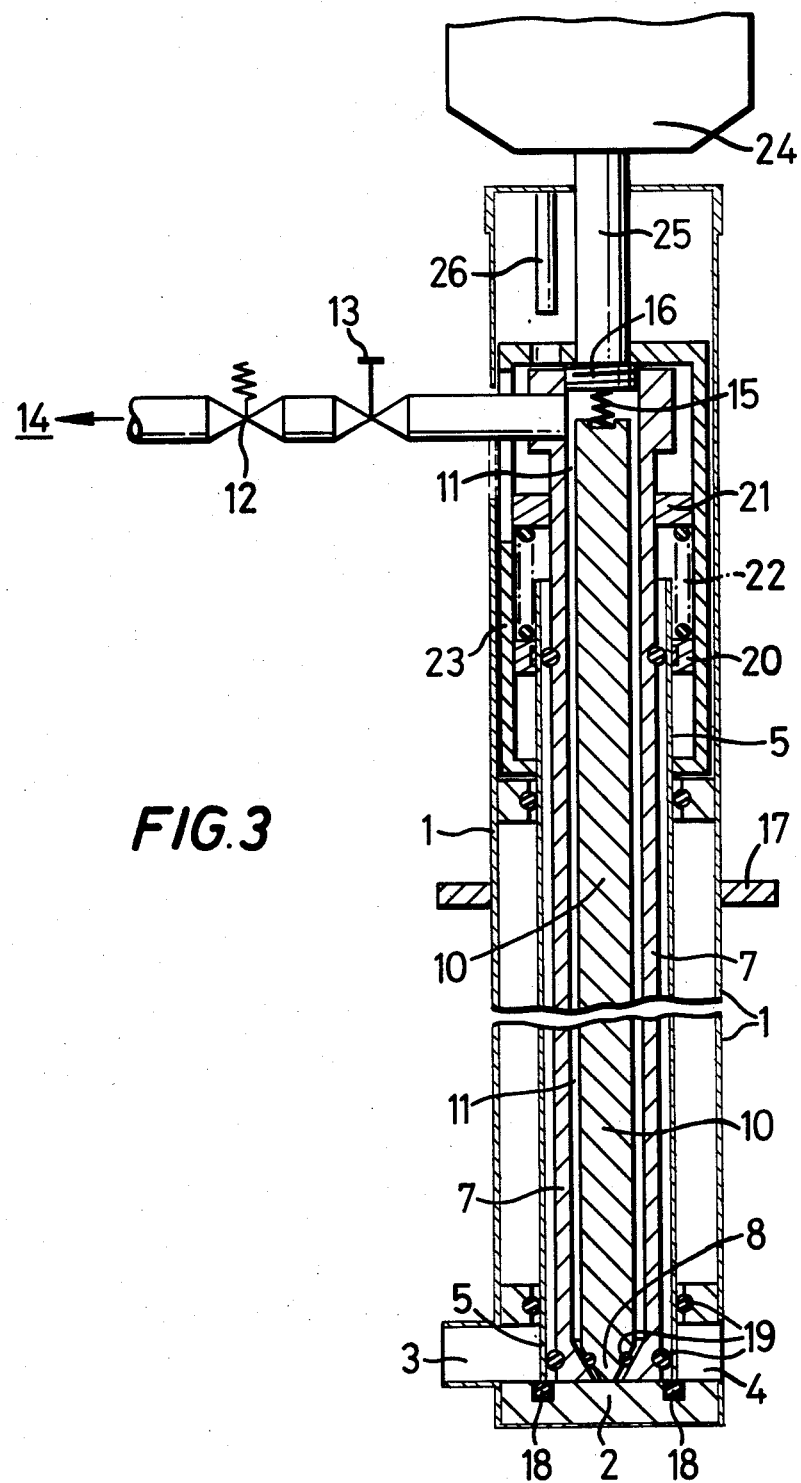
FIG. 3 represents a sectional view of the device with both the sleeve and the piston in the descended position.
Figure 4:
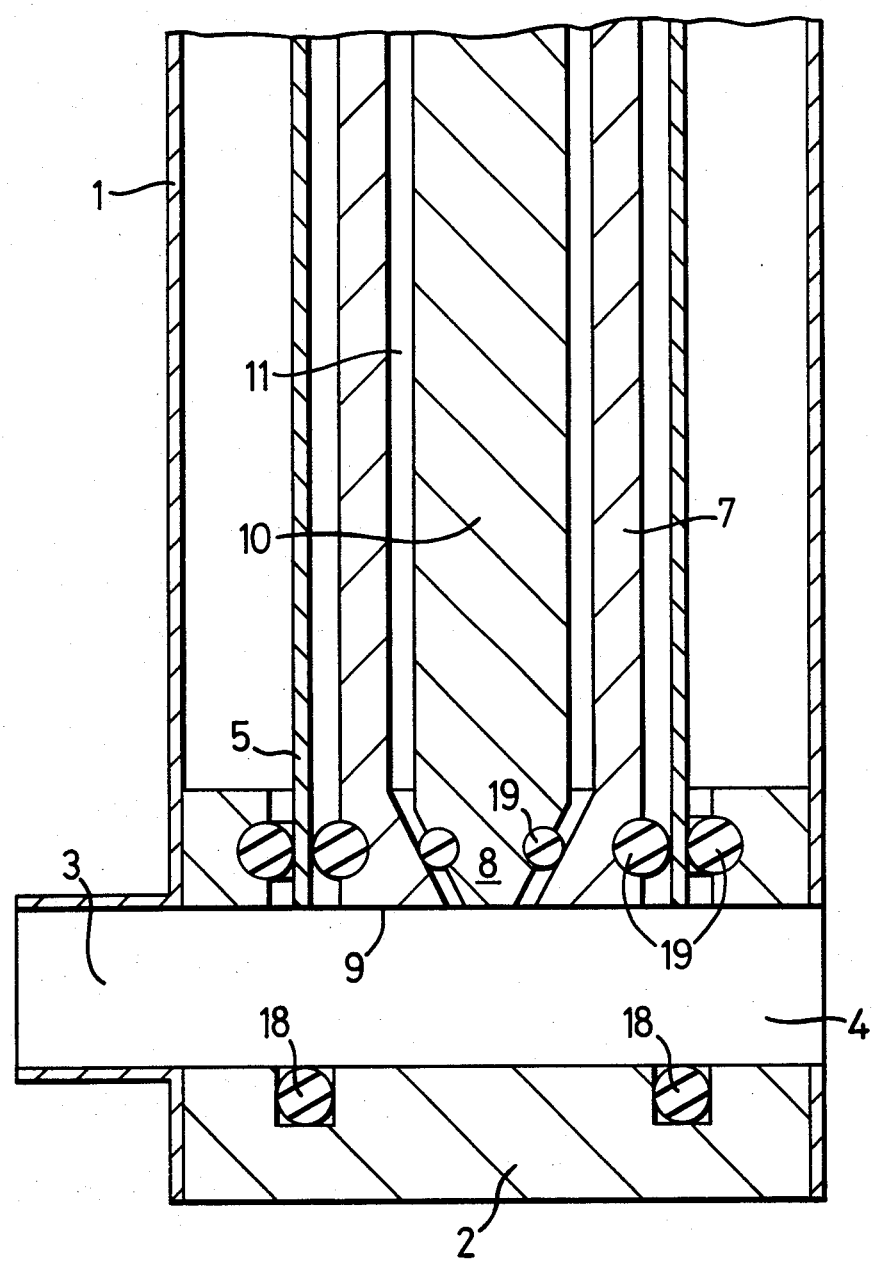
FIG. 4 represents an enlarged sectional view of the lower part of the device in the normal open position as shown in FIG. 1.

In the drawings the outer cylindrical body (1) has adjacent to its base (2) a liquid inlet in the form of a streamlined mouthpiece (3) and a liquid outlet (4). Within the body (1) is a slideably mounted concentric sleeve (5) which causes, when it is lowered to the base (2), the inlet and outlet to be closed defining a chamber (6). Concentric with the sleeve (5) is a removable hollow piston (7) and a detachable non-return valve (8) at the base (9) thereof. The non-return valve (8) has an elongated stem (10) extending to the top of the piston (7) so as to define an internal annulus (11) between the stem and the piston. The annulus (11) is connected at the top to a relief valve (12) through a shut off valve (13) and the relief valve in turn leads to a sample collection point (14). A spring (15) attached to valve stem (10) enables the non-return valve (8) to be held in its normal closed position. The spring (15) abuts against the removable screw threaded head (16) of the piston. The outer body (1) has a flange (17) for securing the device to the pipeline. The points of contact between the lower extremity of the sleeve (5) and the base (2) of the body are provided with base seals (18). Primary O-ring seals (19) are also provided between the body (1) and the sleeve (5) and between the piston (7) and the non-return valve (8) so that the chamber (6) defined by the sleeve (5), the body base (2) and the piston base (9) is liquid-tight. The sleeve (5) and the piston (7) are each provided with a collar (20) and (21) respectively, and a compression spring (22) acting between the sleeve (5) and the piston (7) is located between the collars (20) and (21). The part of the device between the head (16) of the piston and the sleeve collar (20) is enclosed in a cage (23) to which is fixed the actuator (24) by means of shaft (25). The actuator (24) has a cyclic operation with a downward stroke and an upward stroke. In the normal open position of the device the sleeve (5) and the piston (7) are held in position above the inlet (3) and outlet (4) by means of the cage (23) engaging beneath the sleeve collar (20) and lifting the sleeve (5) so as to compress the spring (22) against the piston (7), the piston being restrained from upward movement by means of stop member (26) on the upper portion of the outer body.

In operation of the sampling device the actuator (24) initiates a downward movement of the cage (23) thus releasing the sleeve (5) and allowing it to move downwards under the action of the compression spring (22), instantaneously closing the body inlet (3) and outlet (4) and trapping a sample within the chamber (6) so formed, the piston (7) remaining against the stop member (26) meanwhile. Further downward movement of the cage (23) causes this to engage with the head of the piston (7), forcing this downwards away from the stop member (26) so as to apply pressure to the sample in the chamber and thereby displacing it through the non-return valve (8) into the annulus (11). This downward movement of the piston (7) at the same time pumps an aliquot of the sample out through the shut off valve (13) and the relief valve (12) into the sample collector (14). Thereafter the actuator (24) is reversed and the cage (23) moves upwards, engaging again with the sleeve (5) and moving this upwards into the open position, at the same time lifting the piston (7) via the compression spring (22) up to the stop member (26), and finally re-compressing the spring (22).

I claim:

1. A device for sampling liquid flowing through a pipeline, said device being adapted to be inserted into the pipeline and comprising:

A. a set of concentric tubular members made up of
  (1) an outer, hollow cylindrical body having a base closing one end thereof and having a radially oriented liquid inlet and liquid outlet adjacent to the base thereof,
  (2) a sleeve mounted within and axially slideable with respect to the outer cylindrical body, and
  (3) a hollow piston mounted within and axially slideable with respect to the sleeve, wherein
    (a) the sleeve is adapted to define a liquid-tight chamber between the walls thereof, the base portion of the body and the piston, and is capable of trapping a sample of liquid within said chamber,
    (b) the piston is provided at the base thereof with an internal non-return valve and is adapted to apply pressure to the trapped sample thereby displacing the sample through the valve into the inside of the piston, and
    (c) the inside of the piston is connected to sample removal means for removal of the sample therein, and
B. acuator means for seq-entially lowering first the sleeve and the the piston so as to isolate and remove a sample of liquid.

2. A device according to claim 1 wherein the inlet and outlet in the cylindrical body are transversely orientated.

3. A device according to claim 1 wherein the actuation of the sleeve and piston in a sequential manner is achieved by a pneumatic actuator.

4. A device according to claim 1 wherein a single stroke by the actuator means is converted into a differential action by means of a compression spring acting between the sleeve and the piston so as to form a lost-motion mechanism.

5. A device according to claim 4 wherein the compression spring is located between collars attached to the sleeve and the piston.

6. A device according to claim 5 wherein in a normal open position of the body inlet and outlet, the sleeve and the piston are held in position above the inlet and outlet by means of a cage engaging with the sleeve and lifting the sleeve so as to compress the spring against the piston, the piston being restrained from upward movement by means of a stop member on the upper portion of the outer body.

7. A device according to claim 1 wherein the non-return valve in the piston is retained in a closed position by means of a spring.

8. A device according to claim 7 wherein the non-return valve is provided with an elongated valve stem extending through the length of the piston so as to form an internal annulus within the piston.

9. A device according to claim 1 wherein the sample removal means comprises a relief valve.

10. A device according to claim 9 wherein the relief valve is externally placed with respect to the outer cylindrical body.

11. A device according to claim 10 wherein a shut-off valve is provided between the inside of the piston and the relief valve.

12. A device according to claim 1 wherein both the non-return valve and the piston are removably mounted.

13. A device according to claim 1 wherein the body inlet is provided with a flow straightening mouthpiece.

14. A device according to claim 1 wherein the actuation of the sleeve and piston in a sequential manner is achieved by an electrical actuator.

15. A device according to claim 1 wherein the actuation of the sleeve and piston in a sequential manner is achieved by a hydraulic actuator.

16. A device according to claim 4 wherein the compression spring is located between shoulders formed on the sleeve and the piston.

17. A device according to claim 5 wherein in a normal open position of the body inlet and outlet, the sleeve and the piston are held in position above the inlet and outlet by means of a yoke engaging with the sleeve and lifting the sleeve so as to compress the spring against the piston, the piston being restrained from upward movement by means of a stop member on the upper portion of the outer body.

* * * * *